United States Patent
Roessler et al.

(10) Patent No.: US 8,133,370 B2
(45) Date of Patent: Mar. 13, 2012

(54) GAS SENSOR

(75) Inventors: Mario Roessler, Dobrá Voda u Českych Budějovic (CZ); Sabine Thiemann-Handler, Stuttgart (DE); Berndt Cramer, Leonberg (DE)

(73) Assignee: Robert Bosch GmbH, Stuttgart (DE)

( * ) Notice: Subject to any disclaimer, the term of this patent is extended or adjusted under 35 U.S.C. 154(b) by 630 days.

(21) Appl. No.: 11/992,511

(22) PCT Filed: Sep. 19, 2006

(86) PCT No.: PCT/EP2006/066478
§ 371 (c)(1),
(2), (4) Date: Apr. 22, 2009

(87) PCT Pub. No.: WO2007/036454
PCT Pub. Date: Apr. 5, 2007

(65) Prior Publication Data
US 2009/0301877 A1    Dec. 10, 2009

(30) Foreign Application Priority Data
Sep. 30, 2005   (DE) .................. 10 2005 047 443

(51) Int. Cl.
*G01N 27/407* (2006.01)
(52) U.S. Cl. ......... 204/426; 204/424; 204/425; 204/431
(58) Field of Classification Search .................. 204/424, 204/425, 426, 431
See application file for complete search history.

(56) References Cited

U.S. PATENT DOCUMENTS

2002/0108856 A1* 8/2002 Kunimoto et al. ............ 204/425
2004/0158410 A1    8/2004 Ono

FOREIGN PATENT DOCUMENTS

| EP | 1167957 | 1/2002 |
|---|---|---|
| GB | 2119933 | 11/1993 |
| JP | 2000-028573 | 1/2000 |
| JP | 2002-243692 | 8/2002 |
| WO | WO 02/059559 | 8/2002 |

OTHER PUBLICATIONS

International Search Report, PCT International Patent Application No. PCT/EP2006/066478, dated Jan. 15, 2007.
Miura, N. et al: "Mixed Potential Type Nox Sensor Based on Stabilized Zirconia and Oxide Electrode", Journal of the Electrochemical Society, Electrochemical Society. Manchester, New Hampshire, US, vol. 143, No. 2, Feb. 1996, pp. L33-L35, XP000196991.

* cited by examiner

*Primary Examiner* — Bruce Bell
(74) *Attorney, Agent, or Firm* — Kenyon & Kenyon LLP

(57) ABSTRACT

A gas sensor for sensing the gas concentration in a measured gas mixture, particularly of a nitrogen compound, having a solid electrolyte which connects a first and a second electrode in an ion-conducting manner, the first electrode having a high activity with respect to oxidation or reduction of the gas component that is to be sensed, and the second electrode having a slight activity in this regard. The influence on the activity with regard to oxidation or reduction of the gas component to be determined, due to free oxygen present in the measured gas mixture, is approximately equally strongly pronounced at both electrodes.

14 Claims, 2 Drawing Sheets

GAS SENSOR

This application is a 371 of PCT/EP06/066478, filed on Sep. 19, 2006.

FIELD OF THE INVENTION

The present invention relates to a gas sensor.

BACKGROUND INFORMATION

Conventionally, for the identification of gas components or for the determination of gas concentration in measured gas mixtures, one may use sensors that are designed based on a solid electrolyte, and are operated on the mixed potential principle. The mixed potential forms between two electrodes connected using the solid electrolyte, and represents a measure for the gas components occurring in the gas mixture that are to be identified.

This mixed potential between the two preferably platinum-containing or oxidic electrodes, which may, if necessary, be combined with additional chemical elements, depending on the field of application, has in part great cross-sensitivities with respect to additional gas components that are not desired to be detected, particularly with respect to oxygen and/or hydrocarbons. This cross sensitivity corrupts the measuring signal, so that in gas components to be identified especially at low concentrations, e.g. <50 ppm, great measuring inaccuracies may be determined by the deviation of the measured value from the value that corresponds to the actual concentration.

SUMMARY

It is therefore an object of the present invention to improve a measuring sensor of the type represented at the outset.

The present invention relates to a gas sensor for detecting a gas concentration in a measured gas mixture, particularly of a nitrogen compound or generally of an oxidizable substance, using a solid electrolyte which combines a first and a second electrode in an ion-conducting manner, the first electrode having a high activity with respect to oxidation or reduction of the gas component that is to be detected, and the second electrode having a low activity in this regard. According to an example embodiment of the present invention, the influence on the activity with regard to oxidation or reduction of the gas component to be determined, due to free oxygen present in the measured gas mixture, is approximately equally strongly pronounced at both electrodes. Because the two electrodes are designed in such a way that the binding or the release of oxygen ions, at the three-phase boundary of the two electrodes with the solid electrolyte and the gas phase, are influenced approximately equally greatly or equally little by the free oxygen present in the measured gas, the mixed potential proportion of the sensor with regard to this, for the evaluation of the gas concentration of the gas component to be determined is negligible to the greatest extent.

It is particularly preferred if the two electrodes have comparatively slightly different activity also with respect to hydrocarbon compounds, in comparison to their activity with respect to the gas that is to be sensed. A sensor that is designed in that manner is consequently able to provide a measuring signal which, compared to the first specific embodiment, has an even lesser cross sensitivity with respect to gas components that are not intended to be determined.

The design of such a sensor provides that the two electrodes have the same gas-sensitive base material. In a particularly advantageous way, the gas-sensitive base material for this purpose may be composed of two chemical elements, such as ternary or quaternary compounds or a cermet having two additional elements, a first interconnection structure between the two chemical elements at the first electrode being able to be developed differently from a second interconnection structure between the two chemical elements at the second electrode. It is thereby possible, for example, to develop the two electrodes to have a differently strong catalytic effect with regard to a gas component, that is to be determined, of a measured gas mixture, so that the one electrode has a very strong activity and the other electrode has a slight activity, preferably even no activity with respect to the gas component that is to be sensed.

In order to reduce the oxygen cross sensitivity, when the same base elements are used to produce the electrodes, their preparation is of substantial importance. It influences the later chemical properties of the respective electrode quite substantially.

For the development of two electrodes having greatly different activity properties with respect to a gas component that is to be detected, but that have a low oxygen cross sensitivity, two different interconnection structures between the two chemical elements are particularly suitable, as they may have been created by galvanic material combination methods or by sintering processes.

This massive reduction in oxygen cross sensitivity and also a clear reduction in the cross sensitivity with respect to hydrocarbons was able to be proven by experiments in which the first electrode had the one, and the second electrode had the other structural development for the combination of two equal chemical elements.

Two preferred chemical elements for the development of the two electrodes using such material combination methods are gold (Au) and platinum (Pt). A sensor constructed using such electrodes is particularly well suited for determining, for instance, $NH_3$, $NO_x$ of the hydrocarbon compounds as gas component of a measured gas mixture.

An additional advantage of a gas sensor designed in that manner is that both electrodes may even be exposed to the measured gas mixture that is to be investigated, for the determination of the concentration. In order to generate a signal reflecting the concentration value of the gas component in the measured gas mixture, no additional electrode is required, nor is a reference gas electrode that is exposed to a reference gas. Consequently, the sensor may be produced using a minimum number of method steps. All that is required to provide a working sensor is the development of a substrate element and the positioning of the two electrodes according to the present invention, as well as a heating element, if necessary, and the respective electrical connecting leads. Such a sensor may, of course, be provided additionally at least partially with a protective layer or the like, in order to achieve a longer service life, or possibly to adapt the sensor to special requirements in their use.

BRIEF DESCRIPTION OF THE DRAWINGS

The present invention is explained in more detail on the basis of the figures and the description referring to them below.

DETAILED DESCRIPTION OF EXAMPLE EMBODIMENTS

Figure 1:
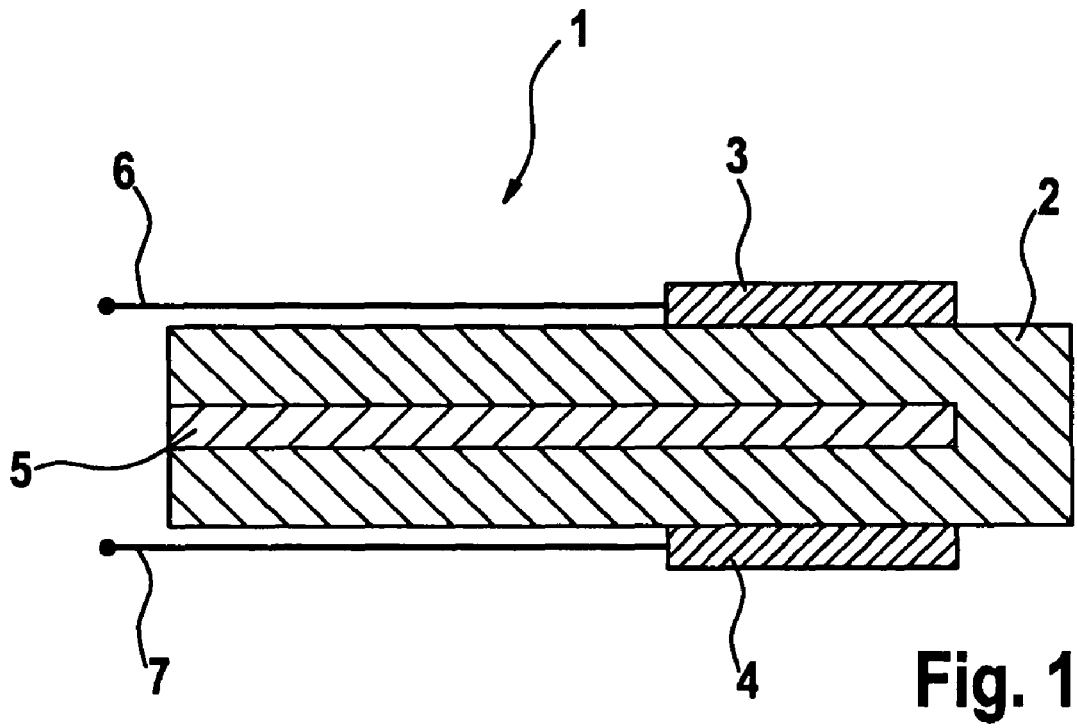
FIGS. 1 & 2 show schematic sectional representations of two differently constructed sensors according to an example embodiment of the present invention.
Figure 2:
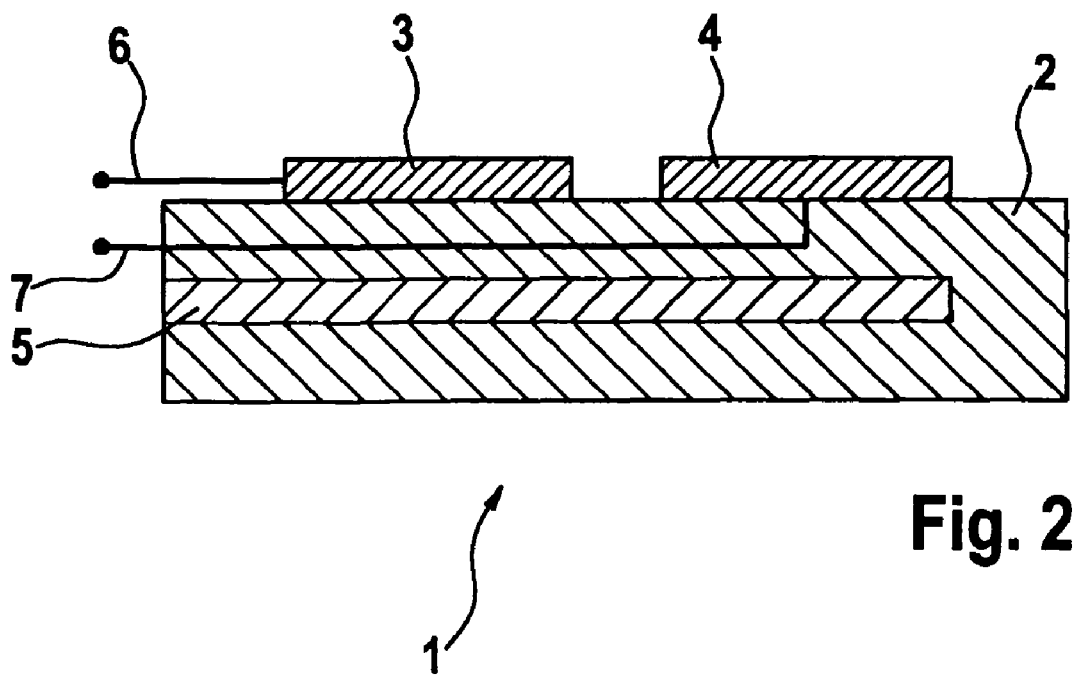

FIGS. 1 and 2 show in detail schematic sectional representations of a sensor 1 according to the present invention in two different specific embodiments. Sensor 1 includes a substrate 2, which is preferably made of yttrium-stabilized zirconium dioxide (YSZ), and which functions at the same time as an ion-conducting electrolyte between the two electrodes 3 and 4 situated on it.

Electrode 3 has a high activity, in this instance, with respect to oxidation or reduction of the gas component that is to be sensed. By contrast, the second electrode has a low activity in this regard. According to an example embodiment of the present invention, both electrodes are developed so that the influence on the activity with regard to oxidation or reduction of the gas component to be determined, due to free oxygen present in the measured gas mixture, is approximately equally strongly pronounced at both electrodes.

Besides this oxygen cross sensitivity which interferes with the measuring signal slightly to not at all, a sensor thus constructed also has a relatively low cross sensitivity with respect to hydrocarbon compounds in comparison to its sensitivity to the gas component that is to be measured.

The two electrodes 3, 4 may be developed for this purpose from the same gas-sensitive base material, this, in turn, being composed of two chemical elements or a cermet having two additional elements.

In one preferred specific embodiment, in this context, the interconnection structure between the two chemical elements of electrode 3 is developed differently from the combination structure between the two chemical elements of electrode 4. It has turned out to be particularly favorable to produce the one interconnection structure between the two chemical elements using a galvanic material combination method, and the second using a sintering process.

For this, the two chemical elements gold (Au) and platinum (Pt) are particularly advantageously suitable. Experiments have established that the electrode whose interconnection structure was produced using the sintering process, which is also called "co-firing", has as good as no influence on the oxidation or reduction of the gas component that is to be sensed. It acts as such a strong catalyst that all components of the gas component that is to be measured, especially $NH_3$, are converted on the surface effective for the recording of the signal, and no significant concentration develops. On such an electrode, the gas component to be sensed has practically no influence on the oxygen activity, and thus on the potential formation.

By contrast, the second electrode, having the galvanically produced interconnection structure between the two chemical elements, which in one particularly preferred specific embodiment is developed as a gilded platinum electrode, has a very sensitive response in this regard, based on its low catalytic activity. The $NH_3$ is not completely converted and reduces the activity of the oxygen at the surface.

Moreover, it is of advantage that both electrodes are able to be exposed directly to the measured gas mixture for determining the concentration of the gas component sought. In the specific embodiment according to FIG. 1, the two electrodes 3, 4 are situated on two opposite sides, above and below solid electrolyte 2 acting as substrate. By contrast, FIG. 2 shows the specific embodiment modified to the extent that both electrodes 3, 4 are developed on the same side of substrate 2. The contacting of the two electrodes is shown symbolically in each case by terminals 6, 7. In order to be able to set the sensor to a certain temperature, which may be a function of the gas component that is to be determined, both sensors according to FIGS. 1 and 2 are furthermore provided with a heating element.

One possible manufacturing method of such a sensor is screen-printing technique in which, for instance, two so-called ceramic foils are used as the front side and the back side of the sensor, between which a heating element may be situated. They, in turn, are each furnished with one of the two measuring electrodes, as shown in the specific embodiment in FIG. 1. To form the one electrode one may use a Pt—Au paste, and a Pt paste to form the other. After a sintering process for the baking and compaction of the sensor element, the Pt electrode may be gilded, for example, using an electrochemical depositing method from an $HAuCl_4$ solution. This develops two electrodes having different interconnection structures between the two chemical elements platinum and gold on the sensor, which effect the advantage according to the present invention, that were proven in experiments.

Figure 3:
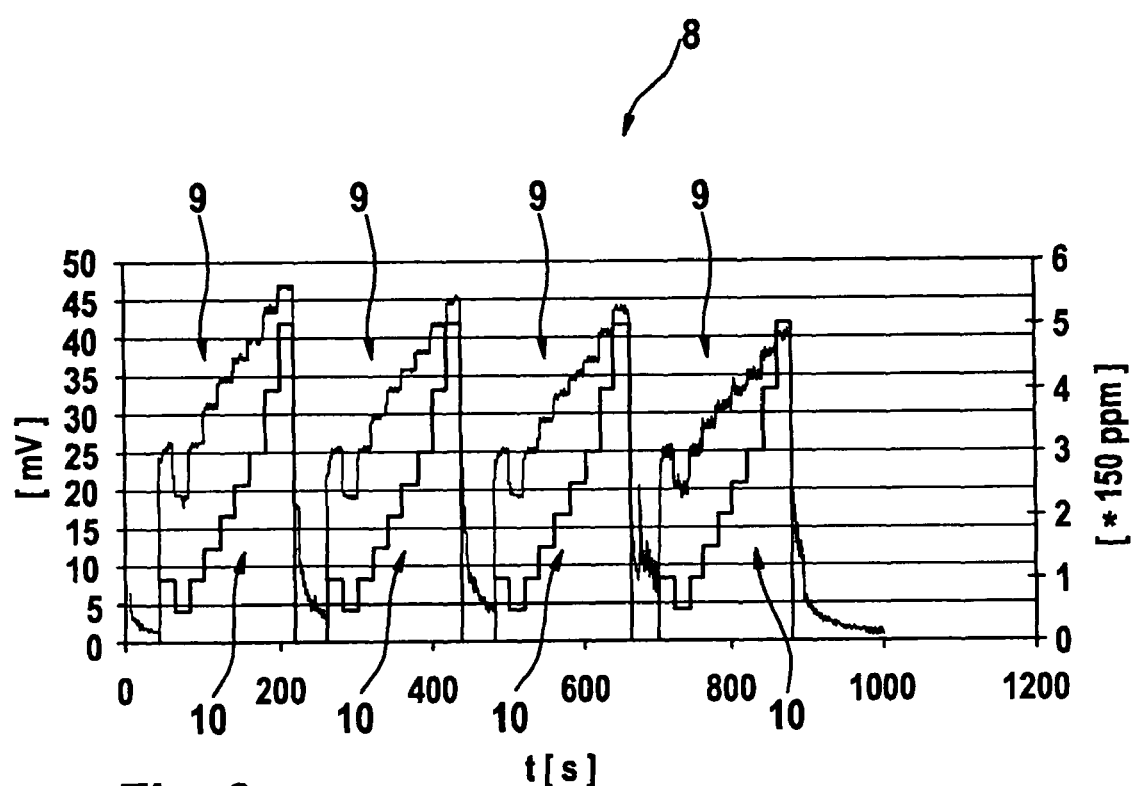
FIG. 3 shows a diagram having measuring signals of the sensor according to an example embodiment of the present invention.

FIG. 3 shows a diagram 8 having a measuring signal 9 in reference to a concentration signal 10 of a gas component of a measured gas mixture. The time t, in seconds, is plotted along the horizontal axis from 0 to 1200. The voltage of the measuring signal, in mV, is scaled from 0 to 50 along the left vertical axis. The right vertical axis represents the concentration of the measured gas component, $NH_3$ in the present case, using the values 0 to 6 to be multiplied by the factor 150 ppm.

The four successive measurements performed were carried out using different oxygen concentrations of 8%, 6%, 4% and 2% (shown from left to right in the figure). In this connection, we particularly point out the high sensitivity of the sensor according to the present invention, at small $NH_3$ flows, and the low oxygen cross sensitivity shown thereby. Only at very low oxygen concentrations is a slight decrease in the signal magnitude to be observed in the sensor according to the present invention, which is loaded with 5 k$\Omega$. Besides the good $NH_3$ sensitivity, this sensor according to an example embodiment of the present invention may also be used outstandingly for determining $NO_x$ gas components, especially $NO_2$ and for a hydrocarbon.

What is claimed is:

1. A gas sensor for sensing a gas concentration in a measured gas mixture, comprising:
   a solid electrolyte which connects a first and a second electrode in an ion-conducting manner;
   a first electrode having a high activity with respect to oxidation or reduction of the gas component that is to be sensed; and
   a second electrode having slight activity with respect to oxidation or reduction of the gas component to be sensed;
   wherein an influence on the activity with regard to oxidation or reduction of the gas component to be sensed is approximately equally strongly pronounced at both electrodes,
   wherein the first electrode has a galvanically interconnected structure and the second electrode has a sintered interconnected structure.

2. The gas sensor as recited in claim 1, wherein the electrodes are configured such that the influence, is due to hydrocarbon compounds or free oxygen present in the measured gas mixture.

3. The gas sensor as recited in claim 1, wherein the gas sensor is adapted to sense the gas concentration in one of a nitrogen compound or a hydrogen compound.

4. The gas sensor as recited in claim 1, wherein the two electrodes have a same gas-sensitive base material.

5. The gas sensor as recited in claim 4, wherein the gas-sensitive base material is composed of two chemical elements.

6. The gas sensor as recited in claim 5, wherein a first interconnection structure between the two chemical elements at the first electrode is developed differently from a second interconnection structure between the two chemical elements at the second electrode.

7. The gas sensor as recited in claim 6, wherein the first interconnection structure is developed as a structure created by a galvanic material combination method.

8. The gas sensor as recited in claim 7, wherein the second interconnection structure is developed as a structure created by a sintering process.

9. The gas sensor as recited in claim 5, wherein one chemical element is gold (Au).

10. The gas sensor as recited in claim 5, wherein one chemical element is platinum (Pt).

11. The gas sensor as recited in claim 5, wherein one chemical element is Pd, Cu, W, V, Ag or Ir.

12. The gas sensor as recited in claim 4, wherein the gas-sensitive base material is composed of ternary or quaternary compounds.

13. The gas sensor as recited in claim 12, wherein a ternary or a quaternary compound is developed differently from a second interconnection structure between the two chemical elements at the second electrode.

14. The gas sensor as recited in claim 1, wherein the two electrodes are configured to supply a measuring signal free from a reference gas relationship.

\* \* \* \* \*